United States Patent [19]
Singh et al.

[11] 4,241,177
[45] Dec. 23, 1980

[54] PROPANOLOL ANTIGEN CONJUGATES AND ANTIBODIES

[75] Inventors: Prithipal Singh, Santa Clara; Marcel R. Pirio, Sunnyvale, both of Calif.

[73] Assignee: Syva Company, Palo Alto, Calif.

[21] Appl. No.: 937,248

[22] Filed: Aug. 28, 1978

[51] Int. Cl.$^3$ .................. C12Q 1/66; C12N 9/96; A61K 39/00; C07G 7/00
[52] U.S. Cl. .................. 435/7; 23/230 B; 424/12; 424/85; 435/188; 260/112 R; 260/121; 564/349
[58] Field of Search ........... 260/112 R, 112 S, 112 B, 260/121, 570.7; 23/230 B; 435/7, 188; 424/8, 12, 85; 536/1; 560/107

[56] References Cited

U.S. PATENT DOCUMENTS

| | | | |
|---|---|---|---|
| 3,337,628 | 8/1967 | Crowther et al. | 260/570.7 |
| 3,690,834 | 9/1972 | Goldstein et al. | 23/230 B |
| 3,817,837 | 6/1974 | Rubenstein et al. | 435/188 |
| 3,878,187 | 4/1975 | Schneider | 424/12 |
| 4,026,879 | 5/1977 | Spector | 424/12 |
| 4,070,492 | 1/1978 | Spector | 424/12 |

OTHER PUBLICATIONS

Smith, "Manufacture of propanolamine derivatives", *Chem. Abstracts*, vol. 67, No. 21, p. 9389 (1967) abs. No. 99907u.

Crowther, et al., "Naphthyl ethanol derivatives", *Chem. Abstracts*, vol. 67, No. 21, p. 9389 (1967) abs. No. 99908v.

*Primary Examiner*—Thomas G. Wiseman
*Attorney, Agent, or Firm*—Betram I. Rowland

[57] ABSTRACT

Compounds are provided which can be used in the preparation of reagents useful for quantitatively determining the presence of $\beta$-adrenergic blocking agents. These compounds contain a derivative of the blocking agent which is linked to an antigen or enzyme, the antigen conjugates being useful for preparing antibodies, and the enzyme conjugates being useful as detectors in an immunoassay as well. Additionally carboxylic acids, esters and aldehydes which are derivatives of the blocking agents are provided which are useful in preparing the above conjugates.

11 Claims, No Drawings

PROPANOLOL ANTIGEN CONJUGATES AND ANTIBODIES

BACKGROUND OF THE INVENTION

1. Field of the Invention

The β-adrenergic blocking agents are pharmacologically active drugs which block the β-adrenergic receptors. Propranolol, the best known member of the class is used to suppress arrhythmia, as well as in the treatment of hypertension. Other β-adrenergic blocking agents which have been studied are dichloroisoproterenol, pronethalol, sotalol, oxprenolol, practolol, and butoxamine.

When these drugs are administered to a patient, it is important to determine the relation between administered dose and in vivo concentration for proper therapeutic response. In order to determine the level of the drug in the blood or other physiological fluid, sensitive tests which distinguish the drug from its metabolites and other concurrently administered drugs are necessary.

Competitive protein binding assays can be used for such determination. For these assays, there is a need for antibodies which are produced at high concentrations, bind to the drug, and only weakly bind to related drugs and metabolites which may be present. These antibodies are prepared using antigenic conjugates of derivatives of the drugs of interest.

Additionally, such assays require a reagent which produces a measurable, reproducible signal in relation to the concentration of drug in the assay medium. This reagent must effectively compete with the drug of interest for antibody binding, and should provide an easily measurable change in signal with small changes of the drug concentration over the concentration range of interest, 10–400 ng/ml in the case of propranolol. Additionally, the reagent should remain stable under assay conditions, and should have a good storage life.

2. Brief Description of the Prior Art

Descriptions of competitive protein binding assays may be found in U.S. Pat. Nos. 3,817,837, 3,850,752, 3,690,834, and in an article by Murphy, 27 J. Clin. Endocr. 973(1967). U.S. Pat. No. 3,875,011 discloses glucose-6-phosphate dehydrogenase conjugates for use in homogeneous enzyme immunoassays.

Preparation of antigenic conjugates and antibodies for a number of different drugs may be found in U.S. Pat. Nos. 3,888,866, 3,766,162, 3,843,696 and 3,878,187, and preparation of certain antigenic conjugates of propranolol derivatives for use in a radioimmunoassay is described in an article by Specter, et al. 196 J. Pharmacol. Exp. Ther. 517–523(1976). See also U.S. Pat. No. 4,070,492, which describes propranolol derivatives substituted at oxygen for the production of assay reagents.

SUMMARY OF THE INVENTION

This invention provides compounds that are conjugates of antigens or enzymes and β-adrenergic blocking agents. The conjugates are useful in homogeneous enzyme immunoassays for the detection of β-adrenergic blocking agents; antigenic conjugates are employed for the preparation of antibodies and enzyme conjugates are employed as detectors. Additionally, carboxylic acids, aldehydes, and esters derived from β-adrenergic blocking agents are provided which are useful in preparing the conjugates.

DESCRIPTION OF THE SPECIFIC EMBODIMENTS

Novel compositions are provided which are derivatives of β-adrenergic blocking agents whereby the amine nitrogen is substituted with a nonoxocarbonylalkyl or oxocarbonylalkyl substituent. The nonoxocarbonyl (including the nitrogen analog) or oxocarbonyl functionality is employed for conjugation to antigens, usually poly(amino acids) or polysaccharides, and enzymes. The antigenic conjugate is employed for the preparation of antibodies which are capable of selection of the subject blocking agent; these antibodies have low cross reactivity to organic compounds of similar structure and are able to bind selectively. In combination with the enzyme conjugate, the antigenic conjugates can be used in homogeneous enzyme immunoassays for the detection of the subject blocking agent. The linking group between the side chain nitrogen atom and the nonoxo- or oxocarbonyl functionality will normally have at least 1 carbon atom and not more than about 10 carbon atoms, preferably having from about 2 to 6 carbon atoms and more preferably 3 carbon atoms. It is normally aliphatic, and may have one or more heteroatoms in the chain, as well as one or more functionalities along the chain.

For the most part, the compounds of this invention will have the following formula:

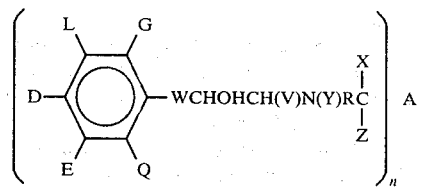

wherein:

G, L, D, E and Q are each hydrogen, aliphatic hydrocarbyloxy (alkoxy or alkenyloxy) containing from 1 to 6 carbon atoms, more frequently 1 to 3 carbon atoms with 0 to 1 site of ethylenic unsaturation (usually methoxy or allyloxy), halo (usually chloro), or acylamido containing from 1 to 3 carbon atoms (usually carboxy or sulfonyl), with the proviso that L can be taken together with G or D to form buta-1,3-dienylene-1,4. Usually not more than 2 of the above symbols are other than hydrogen.

W is oxymethylene, wherein the oxygen is linked to the ring, or a bond.

V is hydrogen or alkyl of from 1 to 3 carbon atoms, usually methyl.

Y is hydrogen or lower alkyl of from 1 to 6 carbon atoms, usually branched, preferably tertiary-butyl or isopropyl.

R is a linking group, preferably an aliphatic linking group, of from 1 to 8 carbon atoms and 0 to 4 heteratoms (oxygen, nitrogen or sulfur), which are usually oxygen, particularly as oxy and nonoxocarbonyl, and may be a branched or straight chain, preferably straight, having from 0 to 1 site of ethylenic unsaturation as the only aliphatic unsaturation, any nitrogen being present as tertiary amino or amido and any sulfur being present as thioether.

A is hydrogen, hydroxy, alkoxy of from 1 to 6 carbon atoms, an antigenic poly(amino acid) or polysaccharide or an enzyme. (The term poly(amino acid), for the purposes of this invention, includes polypeptide residues, proteins, and polypeptide subunits of proteins, which may be in combination with other functional groups such as porphyrins, as in hemoglobin or cytochrome oxidase.)

N is on the average from 1 to the molecular weight of A divided by 1000, usually 1500, with the proviso that n is 1 when A is hydrogen, hydroxy, or alkoxy.

X and Z are taken together to form oxo or imino (NH) or can each be hydrogen if A is an antigenic poly(amino acid) or an enzyme.

The preferred poly(amino acid) compounds will usually be of the following structure

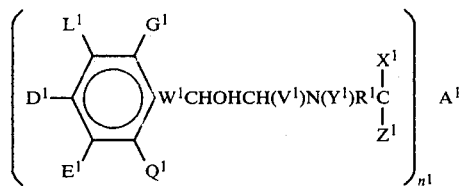

wherein:

$W^1$ is oxymethylene, wherein the oxygen is linked to the ring, or a bond.

When $W^1$ is oxymethylene, each of the other symbols linked to the ring is hydrogen except that either $G^1$ and $L^1$ are taken together to form buta-1,3-dienylene-1,4 (the two rings define naphthyl), or $D^1$ is acetamido, or $Q^1$ is allyloxy.

When $W^1$ is a bond, each of the other symbols linked to the ring is hydrogen except that either $L^1$ and $D^1$ are both chloro, or $L^1$ and $D^1$ are taken together to form buta-1,3-dienylene-1,4, or $G^1$ and $E^1$ are both methoxy.

$V^1$ is usually hydrogen but is methyl when $W^1$ is a bond and $G^1$ and $E^1$ are both methoxy.

$Y^1$ is usually hydrogen or isopropyl, but is tertiarybutyl when $V^1$ is methyl.

$X^1$ and $Z^1$ are each hydrogen or are taken together to form oxo.

$R^1$ is alkylene of from 1 to 4 carbon atoms, either straight or branched chain, and preferably of from 2 to 3 carbon atoms.

$A^1$ is an antigenic poly(amino acid) or an enzyme.

$n^1$ is on the average from 1 to the molecular weight of $A^1$ divided by 1000. If $A^1$ is antigenic, $n^1$ is generally from about 1 to 500, and preferably is about 2 to 75. When $A^1$ is an enzyme, $n^1$ is usually about 1 to 30, and preferably is in the range of about 2 to 12.

Illustrative groups for $R^1$ are methylene, ethylene, ethylidene, propylene, methylethylene, butylene, hexylene, 3-aza-4-oxopentylene, and 2-butenylene.

The preferred compounds which can be used as precursors to the antigen- and enzyme-conjugates of this invention will usually be of the following structure:

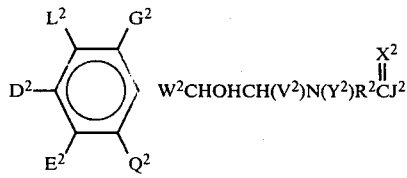

wherein:

$W^2$ is oxymethylene, wherein the oxygen is linked to the ring, or a bond.

When $W^2$ is oxymethylene, each of the other symbols linked to the ring is hydrogen except that either $G^2$ and $L^2$ are taken together to form buta-1,3-dienylene-1,4, or $D^2$ is acetamido, or $Q^2$ is allyloxy.

When $W^2$ is a bond, each of the other symbols linked to the ring is hydrogen except that $L^2$ and $D^2$ are both chloro, or $L^2$ and $D^2$ are taken together to form buta-1,3-dienylene-1,4, or $G^2$ and $E^2$ are both methoxy.

$V^2$ is usually hydrogen but is methyl when $W^2$ is a bond and $G^2$ and $E^2$ are both methoxy.

$Y^2$ is usually hydrogen or isopropyl, but is tertiarybutyl when $V^2$ is methyl.

$X^2$ is oxo.

$R^2$ is the same as R. Preferably it is alkylene of from 1 to 4 carbon atoms, and more preferably of from 2 to 3 carbon atoms.

$J^2$ is hydrogen, hydroxy, or alkoxy of from 1 to 6 carbon atoms, usually 1 to 3 carbon atoms, e.g. ethoxy.

The antigenic poly(amino acids) which may be used in this invention will vary widely as to molecular weight and nature of the poly(amino acid). The amino groups which provide the sites for linking will generally be present as terminal amino groups, as well as present in lysine, arginine, and histidine.

Various protein types may be employed as the antigenic material. These types include albumins, serum proteins, e.g. globulins, ocular lens proteins, lipoproteins, etc. Illustrative proteins include bovine serum albumin, keyhole limpet hemocyanin, egg ovalbumin, bovine gamma globulin, etc. Alternatively, synthetic poly(amino acids) may be prepared having a sufficient number of available amino groups e.g. lysines.

It is particularly useful for A or $A^1$ to be an enzyme which will act as a detector in an immunoassay system, although enzymes will function as antigenic material as well, but will not normally be employed as such.

For use in an immunoassay, a number of characteristics of the enzyme can be considered, e.g., substrates, cofactors, specificity, ubiquitousness, stability to temperature, pH optimum, turnover rate, and the like. Additional factors to be considered are the commercial availability of the enzyme, and the existence of already-developed reproducible assays.

In choosing an enzyme for commercialization, as compared to single or limited use for scientific investigation, there will be a number of desirable criteria. These criteria are set forth in U.S. Pat. No. 3,817,837.

Particularly useful enzymes are the oxidoreductases and the hydrolases. When A or $A^1$ is an oxidoreductase, it will generally be a dehydrogenase, more usually a dehydrogenase dependent on nicotinamide adenine dinucleotide (NAD) or its phosphate, (NADP), and even more usually a dehydrogenase also dependent on a CHOH substrate. More specifically, the enzyme may be malate dehydrogenase or glucose-61-phosphate dehydrogenase (G6PDH). Hydrolases of particular interest include lysozyme, alkaline phosphatase and β-galactosidase.

While various sources of G6PDH may be employed, a particularly desirable source for the subject compounds is the bacterium L. mesenteroides. The particular value of the G6PDH from this bacterium is that it is able to utilize NAD. Therefore, one can limit interference from endogenous G6PDH (which cannot utilize NAD) by employing NAD as the co-factor, when the subject compounds are used in immunoassays.

To form the compounds of the subject invention, a number of methods can be employed.

Where the final product is formed by linking the nonoxocarbonyl functionality to the antigen or enzyme by an amide linkage, mixed anhydrides, particularly monoalkyl carbonate esters, carbodiimides or active esters e.g. N-hydroxy succinimide or p-nitrophenyl, may be employed for activating the carboxyl group. For amidine formation, alkyl imidates are satisfactory. For polysaccharides, linkage will be at hydroxyl groups and the same carboxyl activators may be employed for formation of esters.

Alternatively, the ester can be converted to the aldehyde using a reagent such as diisobutyl aluminum hydride. The aldehyde can then be conjugated to an amino group of the antigen or enzyme at the terminal carbon by reductive amination with a borohydride.

The antibodies which are prepared in response to the conjugated antigens made in the above manner have strong specific binding to the parent drug as well as the enzyme conjugates used for the immunoassay.

(The following examples are offered by way of illustration and not by way of limitation. All temperatures not indicated are in Centigrade.).

EXPERIMENTAL

EXAMPLE 1

Preparation of N-carbethoxypropenyl propranolol

A. Into a stirring solution of 100 mg, (0.386 mmole) of propranolol and 1 ml of anhydrous tetrahydrofuran was added 74.5 mg. (0.386 mmole) of freshly distilled ethyl bromocrotonate, 75% tech, at ambient temperature. The reaction was monitored by tlc analysis (silica gel GF eluant, 20% methanol-benzene). Within a few hours a white precipitate developed. 39 mg of ethyl bromocrotonate was added and the reaction was continued for 20 hours, at which time the solution was placed in a separatory funnel, 100 ml of water was added and the pH was adjusted to alkaline with aqueous NaOH. The aqueous phase was extracted with four 25 ml portions of chloroform. The organic phase was washed with saturated brine, and dried with $MgSO_4$. The solvent was removed on rotavap, affording a crude residue, of 0.144 g.

The residue was chromatographed on preparative tlc silica gel PF-254, eluant 20% methanol-benzene, on two 20×20 cm plates. The appropriate bands were combined, and the material was extracted with methanol. Evaporation of the filtrate yielded 110 mg (yield: 75%).

EXAMPLE 2

Formation of N-carbethoxypropyl propranolol

In a 250 ml hydrogenation vessel was placed 1.37 gm (0.0036 mole) of the product of Example 1 dissolved in 75 ml absolute ethanol, and 100 mg of 5% palladium on powdered charcoal. The solution was evacuated with a water aspirator, flushed with nitrogen and then subjected to 35 psi hydrogen while shaking on a Parr-apparatus for 2.0–2.5 hours. The solution was then filtered through a Celite pad and the filtrate was evaporated leaving 1.3 g of a light yellow oil.

The oil was purified on preparative tlc plates (silica gel PF-254, 20×20 cm, eluant 10% methanol-benzene.) The appropriate bands were detected under a short wavelength UV lamp, combined, and extracted with 50% methanol-chloroform. The filtrate was evaporated on rotavap and dried under vacuum, yielding 1.2 gm of a colorless oil.

EXAMPLE 3

Saponification of N-carbethoxypropyl propranolol to N-carboxypropyl propranolol

In a solution of 10 ml 1 N NaOH, 30 ml methanol, 10 ml tetrahydrofuran and 700 mg (1.87 mmoles) of ester was dissolved and stirred with a teflon bar at room temperature for 2 hours. The mixture was then neutralized with 10% HCl while monitoring with a pH meter. At this point the aqueous solution was extracted with five 30 ml portions of chloroform dried with $MgSO_4$ and filtered. The solvent was removed on rotavap and under vacuum, and afforded a light yellow foam.

The product was purified by dry column chromatography. A glass column 2.5 cm × 35 cm was packed with 60 gm of dry silica gel G80-200 mesh, equilibrated with 10% by weight of the eluant, (1:1 methanol-benzene) and the acid was deposited on the column top. The total volume of solvent used was approximately 500 ml; 30 ml was collected. Tlc (silica gel GF, eluant 50% methanolbenzene) revealed the fractions containing the desired product; they were pooled and concentrated. The weight of the recovered acid was 600 mg.

EXAMPLE 4

Conjugation of N-carboxypropyl propranolol to Bovine Serum Albumin (BSA) and Bovine gamma Globulin (BgG).

A. Conjugation to BSA

Into a 5 ml round bottom flask equipped with a $CaCl_2$ dry tube was placed 150 mg (0.437 mmole) of dried product of Example 3 (N-carboxypropyl propranolol), 50 mg (0.437 mmole) of N-hydroxy succinimide and 2 ml anhydrous THF. The contents were cooled in an ice bath (0°–5°) and stirred with 90 mg (0.437 mmole) of dicyclohexylcarbodiimide. Within 30 minutes a precipitate appeared (dicyclohexyl urea). The mixture was stirred at 5° in a cold room for a total of 22 hrs. The solution of NHS-ester was passed through a glass wool filter and added dropwise to a stirring 5° solution of 0.5 gm ($7.8 \times 10^{-6}$ mole) of BSA (Miles lot #36) in 40 ml of $Na_2CO_3$—$NaHCO_3$ buffer, pH 9.8. The resulting solution was stirred for 20 hours. This conjugate solution was then centrifuged for 20 minutes at 10,000 RPM, the supernatant dialyzed in a cylinder (m.w. cutoff 6,000–8,000; dia: 14.6 mm) and treated with three successive solvent changes of 6 liters $NH_4OH$—$H_2O$, pH 9.6, for 4 hours, 4 hours, and overnight respectively. The dialyzed solution was passed through a 0.22 $\mu M$ millipore filter into a sterilized lyophilization flask (300 ml). The yield upon drying was 440 mg of the BSA conjugate. The hapten number was 16.

B. Conjugation to BgG

A solution of 180 mg (0.522 mmole) of the product of Example 3 (dried at 60° under vacuum overnight), 60 mg (0.522 mmole) of N-hydroxy succinimide (crystals from EtOAc), 107 mg (0.522 mmole) dicyclohexylcarbodimiide (previously distilled) and 1 ml of anhydrous DMF (distilled over $CaH_2$), in a 5 ml round bottom flask was stirred with a teflon bar for 20 hours at 5°. After a few hours a precipitate was observed.

After passing the above NHS-ester solution through a glass wool plug into a stirring solution of 0.5 g BgG (F.II Miles lot 57) in 40 ml of $Na_2CO_3$—$NaHCO_3$ buffer, pH 9.6, at 0°–5°, the final solution was transferred to a cold room overnight, and then dialyzed with 6 liters NH$_4$OH—H$_2$O, pH 9.6, for 4 hours each, and 1 liter NH$_4$OH—H$_2$O, pH 9.6, overnight.

The residue in the dialysis bag was centrifuged at 10,000 RPM for 20 minutes and the supernatant was decanted onto a 0.22 μM millipore filtration apparatus, and external pressure was applied. The filtrate was collected in a sterilized (300 ml) lyophilization flask, frozen and lyophilized.

The yield was 220 mg of the conjugate. The hapten number measured by UV analysis was 18.

EXAMPLE 5

Formation of N-(4-oxobutyl-1) propranolol.

Into a 25 ml three-neck round bottom flask equipped with a center serum cap was placed 600 mg (1.6 mmole) of dry product of Example 2 and 15 ml of anhydrous toluene, under dry nitrogen. This was stirred with a teflon coated bar in a dry ice acetone bath ($-70°$). To this was added dropwise via syringe, 1.0 ml of AlH(isoC$_4$H$_9$)$_2$ (95% pure, 20% by weight in hexane, Alfa product Ventron). The reaction medium was monitored on tlc silica gel GF-methanol. After 0.5 hr. a new spot appeared corresponding to the aldehyde and after one and two hour intervals 0.5 ml more of reducing agent was added (total volume of AlH(isoC$_4$H$_9$)$_2$, 2.5 ml).

The reaction was stirred another hour and then quenched with saturated sodium bisulfite, extracted with chloroform (three 50 ml portions) and filtered to remove aluminum salts. The aqueous phase was made alkaline with NaOH pH 9.0, extracted with three 50 ml portions of chloroform, and the combined extracts were dried with MgSO$_4$. The solvent was removed on a rotavap and the product dried under vacuum, yielding 450 mg, 85% of aldehyde (tlc analysis, silica gel GF, 10% methanol-benzene).

EXAMPLE 6

Conjugation of N-(4-oxobutyl-1) propranolol to BSA by reductive amination with sodium cyanoborohydride.

In 50 ml of sodium phosphate buffer (Na$_2$HPO$_4$—NaH$_2$PO$_4$), pH 9.0, 500 mg of miles BSA lot 36 was dissolved and cooled in an ice bath. To this was added dropwise a solution of 2 ml DMF and 120 mg of the product of Example 5, and then 120 mg of sodium cyanoborohydride. The solution became turbid and a light brown precipitate formed. After 2.5 days at 5° with continuous stirring, the contents were transferred into dialysis cylinders (m.w. 6000–8000, dia. 14.6 mm) and treated with successive changes of solvent three times with 4 liters of distilled water for 4 hours each.

The antigen solution was passed through a Sephadex-50 column; the appropriate fraction was combined and passed through a 0.22 μM millipore filter with difficulty (external pressure applicable) into a 300 ml sterilized lyophilization flask. The weight of the product was 250 mg.

The 250 mg of the above product and 200 mg of BSA were combined and dissolved in 40 ml of Na$_2$HPO$_4$—NaH$_2$PO$_4$ buffer, pH 7.2, and 20 ml of DMF. The solution was cooled in an ice-bath and stirred. 152 mg of the product of Example 5 in 3 ml DMF was added dropwise and the protein solution became turbid. Then 120 mg of sodium cyanoborohydride was added. The reaction mixture was kept at 5° in a cold room for 3 days.

The solution of conjugate was centrifuged at 10,000 RPM for 25 min. The liquid was decanted into a lyophilization flask and frozen. The solvent was reduced to 40 ml and passed through a Sephadex-50 column (250 ml volume) eluted with distilled water. 25 ml increments were collected and fractions 3 through 5 were combined and passed through a 0.22 μM millipore filter into a 300 ml sterilized flask and lyophilized. UV determination revealed a hapten number of 10. The weight was 200 mg.

EXAMPLE 7

Conjugationa of Glucose-6-phosphate dehydrogenase (G6PDH) to N-carboxypropyl propranolol.

Two separate batches of ester were prepared by introducing 12.1 mg of N-carboxypropyl propranolol (35 mmoles), 4.2 mg of N-hydroxy succinimide (36.8 mmoles) (NHS) and 7.73 mg of ethyl dimethylamino carbodiimide (EDAC) in 350 μl tetrahydrofuran into a first flask and introducing the same reactants in the amounts of 24.2 mg, 8.4 mg, and 15.5 mg in 700 μl dimethyl formamide, respectively, into a second flask. The acid and NHS were combined first and cooled to 4°, followed by the addition of EDAC. After standing overnight, the temperature was raised to room temperature and the reaction allowed to proceed overnight.

The enzyme glucose-6-phosphate dehydrogenase (G6PDH) was then conjugated as follows.

In a reaction flask were combined 2 ml of G6PDH (Beckman, 3 mg/ml protein), 40 mg glucose-6-phosphate (G-6-P), 80 mg NADH and two additions of 300 μl carbitol. After an initial addition of 25 μl of the crude ester solution prepared above, 50 μl aliquots were added with a final 25 μl aliquot for a total of 400 μl over a 2 hour and 35 minute period. A total of 690 μmoles of the ester were added per μmole of enzyme. At the end of the time the enzyme was 48% deactivated and about 55% inhibited when saturated with antibody.

The reaction mixture was centrifuged at 19,000 RPM at 4° for 30 min and the supernatant chromotographed on a Sephadex G-50 column (~180 ml), equilibrated, and eluted with tris-HCl (55 mM, pH 8), with 2.6 ml fractions collected.

The column was then washed with 500 ml buffer. (Preferably, a new column should be prepared.) The enzyme-containing fractions were pooled, concentrated to 6 ml, and chromatographed as described previously. The total volume of pooled fractions collected was 15.5 ml.

EXAMPLE 8

Preparation of 1,2-epoxy-3-(1'-naphthoxy)propane.

To 55.3 g (0.38 mole) of α-naphthol was added with stirring ring 15.5 g of sodium hydroxide in 55 ml of water, the mixture cooled to 10° and 35.5 g epichlorohydrin added dropwise. After stirring for about 18 hrs, the solution was extracted with 2×200 ml chloroform, washed twice with water and dried over MgSO$_4$. Tlc showed the reaction had not gone to completion.

EXAMPLE 9

Preparation of N-(3'-(1''-naphthoxy)-2-hydroxypropyl)-alanine methyl ester.

Into a reaction flask was introduced 600 mg (3 mmole) 1,2-epoxy-3-(1'-naphthoxy)propane, 418 mg (2.9 mmole) D,L-alanine methyl ester hydrochloride and 316 mg (3 mmole) of sodium carbonate in 30 ml of dry methanol. The mixture was stirred with refluxing for two days. Tlc on silica gel with 10% methanol-90% chloroform provided about 100 mg of product.

The preparation of the desired compound was repeated using a somewhat different procedure. D,L-alanine methyl ester hydrochloride (2 g) was neutralized by dissolving in water made alkaline with 1 N sodium hydroxide, the solution extracted with chloroform, the chloroform solution dried over magnesium sulfate and the solution concentrated at room temperature. The concentrate was then added to a solution of 565 mg of 1,2-epoxy-3-(1'-naphthoxy)propane in 20 ml tetrahydrofuran and the mixture refluxed for four days. After cooling the reaction mixture and concentrating in vacuo, the reaction mixture was chromatographed using 10% methanol-90% chloroform as eluant. The product was extracted from the plate with chloroform and the solution concentrate. Yield: 450 mg, 56%.

EXAMPLE 10

Preparation of N-(3'-(1''-naphthoxy)-2'-hydroxypropyl-1')alanine.

To a reaction flask was added 400 mg (1.4 mmole) of the ester of Example 9, 20 ml of 1 N aqueous sodium hydroxide, 20 ml methanol and 10 ml tetrahydrofuran and the mixture stirred overnight at room temperature. The solution was brought to pH 6.8 with dilute hydrochloric acid and the solution evaporated to dryness in vacuo. The residue was extracted with chloroform, the solution filtered and the filtrate concentrated to leave 270 mg of a dry white solid of the desired product.

The above acid can be conjugated by known means to proteins to produce antigenic conjugates which can be used for the preparation of antibodies specific for propranolol or conjugated to enzymes, particularly dehydrogenase enzymes, such as glucose-6-phosphate dehydrogenase and malate dehydrogenase or to hydrolases, such as glycosidases e.g. beta-galactosidase, for immunoassay reagents.

Antibodies were prepared employing the conjugates of Examples 4 and 6 in accordance with known procedures. The bleeds were harvested and the antibodies isolated according to known techniques.

The following is the assay procedure employed for the determination of the presence of propranolol.

In carrying out the propranolol assay, a number of reagent solutions are prepared:

Basic Buffer
0.055 M Tris-HCl
0.05% Sodium Azide
0.005% Thimerosal
pH 8.1 at room temperature
Assay Buffer
Basic Buffer
0.5% NaCl
0.01% Triton X-100
pH 8.1 at room temperature
Substrate/Antibody Diluent
Basic Buffer
1.0% RSA (Rabbit Serum Albumin)
0.04 M NAD
0.066 M glucose-6-phosphate
pH 5.0 at room temperature
Enzyme Diluent
Basic Buffer
1.0% RSA
0.9% NaCl
pH 8.1 at room temperature Antibody-Substrate Reagent A Antibody Substrate is used to dilute gamma globulin isolated as above so that ca 70% of the G6PDH conjugate activity is inhibited in the assay solution.

Enzyme Reagent B

The enzyme conjugate (e.g., Example 7) is diluted with enzyme diluent to attain the desired maximum rate. This is measured by aspirating into a spectrometer and taking the change in readings at 340 nm over a 30 second period after a 15 second delay.

In carrying out the assay, the assay solution is prepared by combining the following: 50 $\mu$l of the sample to be assayed, 50 $\mu$l of Reagent A, and 50 $\mu$l of Reagent B with 750 $\mu$l of assay buffer. The mixture is aspirated into a spectrometer and the $\Delta$ OD read at 340 nm. The concentration of propranolol in the sample is read from a standard curve prepared by using standardized solutions and taking readings.

The drugs listed below were used in preliminary testing for cross-reactivity with propranolol using the assay procedure described above: 4-hydroxypropranolol (4 POH), N-desisopropyl-propranolol (DIPP), propranolol glycol (PG), naphthoxylactic acid (NLA), and naphthoxyacetic acid (NAA). All are metabolites of propranolol itself. The latter two compounds exhibit no interference. The remainder show cross reactivity as below.

| | CROSS-REACTIVITY* | | |
|---|---|---|---|
| | Antibodies prepared from BSA conjugate according to Example 6 | | Antibodies prepared from BgG conjugate according to Example 4 |
| | Lot | Lot | Lot |
| | 2216 | 2215 | 2153 |
| 4POH | >1µg/ml | >1µg/ml | 190ng/ml |
| DIPP | 200ng/ml | 22ng/ml | 8ng/ml |
| PG | 400ng/ml | 230ng/ml | 84ng/ml |

*Expressed as the concentration necessary to elevate the signal of a 100ng/ml standard solution by 30%.

In the above assay, coefficients of variation of standard solutions using antibodies prepared from a BSA conjugate prepared as in Example 6 and a BgG conjugate prepared as in Example 4 are a maximum of 17% at 25 ng/ml of propranolol, 8% at 100 ng/ml propranolol, and 6% at 400 ng/ml propranolol.

The foregoing data illustrates that the compounds of the subject invention are effective in providing reagents which are useful in immunoassays for the determination of the $\beta$-adrenergic blocking agents, particularly propranolol. In addition, the antibodies which are provided are able to detect the presence of the blocking agents, especially propranolol, so that the subject assay can be used to provide a rapid determination of the concentration of these compounds in the blood.

The subject $\beta$-adrenergic blocking agents are for the most part difficult to conjugate. The problems of preparing appropriate conjugates which may be used for the production of antibodies are overcome by employing the compounds of the subject invention. The antibodies produced using the conjugated antigens of the subject invention are found to provide the desired high binding constants for the desired group of compounds.

Although the foregoing invention has been described in some detail by way of illustration and example for purposes of clarity and understanding, it will be obvious that certain changes and modifications may be practiced within the scope of the appended claims.

What is claimed is:

1. A compound of the formula:

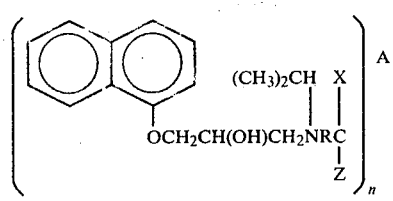

wherein:

R is an aliphatic linking group of from 1 to 4 carbon atoms;

X and Z are taken together to form oxo or can each be hydrogen;

A is an antigenic poly(amino acid) or an enzyme;

n is on the average from 1 to the molecular weight of A divided by 1000.

2. A compound according to claim 1 wherein A is an antigenic poly(amino acid).

3. A compound according to claim 1 wherein A is an enzyme.

4. A compound according to claim 3 wherein said enzyme is glucose-6-phosphate dehydrogenase.

5. A compound of the following formula:

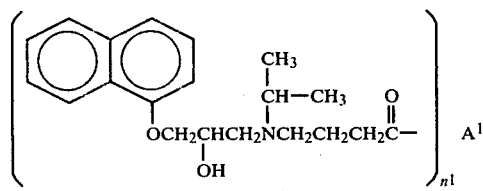

wherein:

$A^1$ is an antigenic poly(amino acid); and $n^1$ is on the average from 1 to the molecular weight of $A^1$ divided by 1000.

6. A compound according to claim 5 wherein said antigenic poly(amino acid) is bovine serum albumin or bovine gamma globulin.

7. A compound of the following formula:

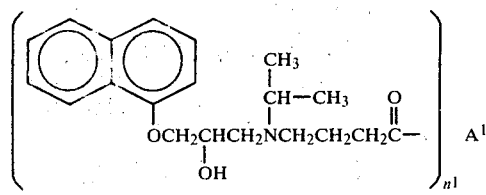

wherein:

$A^1$ is an enzyme; and $n^1$ is on the average from 1 to the molecular weight of $A^1$ divided by 1000.

8. A compound according to claim 7 wherein said enzyme is glucose-6-phosphate dehydrogenase.

9. A compound of the formula

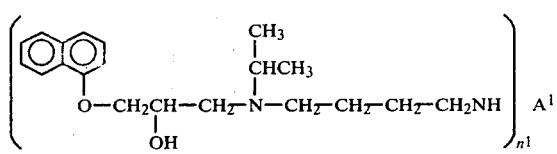

wherein $A^1$ is an antigenic poly(amino acid) or enzyme; and $n^1$ is one to the molecular weight of $A^1$ divided by 1,000.

10. An antibody prepared by administering to a host animal an antigen conjugate of a propranolol derivative having the formula of claim 1, and which has sites capable of specifically binding to propranolol.

11. A method for determining the presence of a drug which is propranolol in a medium suspected of containing said drug which comprises:

forming, at a pH in the range of about 5–10 and at a temperature of from about 10°–50° C., an aqueous solution of said medium, an enzyme conjugate of said drug according to claim 1, and antibody having sites capable of binding to said drug and said enzyme conjugate, said antibody being at a sufficient concentration to substantially reduce the enzymatic activity of said enzyme conjugate in the absence of said drug; and analyzing said solution for the enzymatic activity of said enzyme conjugate in said solution.

* * * * *